(12) United States Patent
Uematsu et al.

(10) Patent No.: US 11,211,150 B2
(45) Date of Patent: Dec. 28, 2021

(54) MASS SPECTRUM PROCESSING APPARATUS AND MODEL GENERATION METHOD

(71) Applicant: JEOL Ltd., Tokyo (JP)

(72) Inventors: Fuminori Uematsu, Tokyo (JP); Takaya Satoh, Tokyo (JP); Masahiko Takei, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 17/004,229

(22) Filed: Aug. 27, 2020

(65) Prior Publication Data

US 2021/0065849 A1 Mar. 4, 2021

(30) Foreign Application Priority Data

Aug. 28, 2019 (JP) .............................. JP2019-155653

(51) Int. Cl.
*H01J 49/00* (2006.01)
*G16C 20/20* (2019.01)

(52) U.S. Cl.
CPC .......... *G16C 20/20* (2019.02); *H01J 49/0036* (2013.01)

(58) Field of Classification Search
CPC ............................ G16C 20/20; H01J 49/0036
USPC ............ 250/281, 282; 702/22–24, 26–28, 32
See application file for complete search history.

(56) References Cited

U.S. PATENT DOCUMENTS

2013/0311109 A1 11/2013 Yao
2020/0065699 A1* 2/2020 Tamai .................... G06K 9/482

FOREIGN PATENT DOCUMENTS

| JP | 2005214799 A | 8/2005 | |
|---|---|---|---|
| JP | 2005257483 A | 9/2005 | |
| JP | 2014112068 A | 6/2014 | |
| WO | 2018134952 A1 | 7/2018 | |
| WO | WO-2018134952 A1 * | 7/2018 | ......... G06K 9/00127 |

OTHER PUBLICATIONS

Polanski et al., Signal Partitioning Algorithm for Highly Efficient Gaussian Mixture Modeling in Mass Spectrometry, PLOS One, vol. 10, No. 7, Jul. 31, 2015, pp. 1-19.
Gan et al., A Novel Approach to the Retrieval of the Mass Spectrum of a Mixture, Analytical Sciences, vol. 16, Jun. 2000, pp. 603-607.
Extended European Search Report issued in EP20191616.0 dated Jan. 22, 2021.

* cited by examiner

*Primary Examiner* — Michael Maskell
(74) *Attorney, Agent, or Firm* — The Webb Law Firm (57) ABSTRACT

A preprocessor extracts a plurality of spectra to be processed, from an overall mass spectrum. A simulated spectrum generator having a learned model generates a simulated spectrum having a peak discriminating action, from each mass spectrum. A postprocessor generates a combined simulated spectrum based on the plurality of simulated spectra. A peak filter executes peak discrimination on a peak list using the combined simulated spectrum.

10 Claims, 12 Drawing Sheets

MASS SPECTRUM PROCESSING APPARATUS AND MODEL GENERATION METHOD

CROSS-REFERENCE TO RELATED APPLICATION

This application claims priority to Japanese Patent Application No. 2019-155653 filed Aug. 28, 2019, the disclosure of which is hereby incorporated by reference in its entirety.

BACKGROUND OF THE INVENTION

Field of the Invention

The present disclosure relates to a mass spectrum processing apparatus and a method of generating a model, and in particular to a peak discriminating technique.

Description of Related Art

A mass spectrum is generated by mass spectrometry performed on a sample. The mass spectrum generally includes multiple mass peaks (hereinafter, the mass peak may also be simply referred to as a "peak"). These mass peaks include, in addition to a plurality of peaks derived from the sample, a plurality of peaks which are not derived from the sample (hereinafter, the peaks derived from the sample will be referred to as "sample peaks", and the peaks not derived from the sample will be referred to as "background noise peaks"). Normally, the background noise peak exists as a noise in a background level range.

In general, there is a tendency that, while the sample peak has a sharp form and a narrow peak width, the background noise peak has no reproducibility in terms of its shape, and has a wide peak width. When a determination is to be made as to whether or not a peak is the sample peak for each peak on a peak list generated from the mass spectrum, reference is made to an m/z value and an intensity of each individual peak. More specifically, normally, reference is made to an m/z value corresponding to a center of gravity of the peak and an intensity determined from a peak area. Although a height of the background noise peak is relatively low, the area is relatively large. Thus, if peaks are to be discriminated based simply on the intensity, it is difficult to accurately distinguish between the sample peak and the background noise peak. When the peak discrimination cannot be appropriately executed, mass spectrometry of a minute-amount component included in the sample becomes difficult.

Although it is possible for an analyst to discriminate with his/her eyes whether each peak included in the mass spectrum is the sample peak or the background noise peak, if all peaks are to be discriminated by such a visual inspection by the analyst, a large burden is placed on the analyst. JP 2014-112068 A discloses a technique for classifying each peak included in the mass spectrum, but this reference does not disclose peak discrimination based on a simulated spectrum.

An advantage of the present disclosure lies in enabling precise discrimination of each of a plurality of sample peaks included in a mass spectrum while resolving or reducing the burden for the analyst. Alternatively, an advantage of the present disclosure lies in provision of a technique for easily generating a learned model for discriminating sample peaks.

SUMMARY OF THE INVENTION

According to one aspect of the present disclosure, there is provided a mass spectrum processing apparatus comprising: a generator configured to generate, by a learned model, a simulated spectrum for discriminating a sample peak from a mass spectrum; and a peak filter configured to extract, from among a group of mass peaks included in the mass spectrum, a plurality of mass peaks corresponding to a plurality of simulated peaks included in the simulated spectrum.

According to the structure described above, an artificial, simulated spectrum which functions as a discriminating spectrum is generated from the mass spectrum. The simulated spectrum is a waveform, a graph, or a sequence of numbers corresponding to the mass spectrum, and includes a plurality of simulated peaks. Each simulated peak is an element for specifying or identifying a mass peak to be extracted, and is an artificial peak. In a peak filter, the simulated spectrum is caused to act on the mass spectrum, to thereby extract a plurality of sample peaks to be extracted. In other words, a plurality of background noise peaks which are not extraction targets are removed.

The simulated spectrum is generated by a learned model in which knowledge and experience of an analyst who analyzes a mass spectrum are reflected and accumulated. In filtering of the mass peak, with the use of such a learned model, a peak discriminating result comparable to or superior to that obtained by the analyst can be expected. According to the structure described above, the occurrence of work and efforts of the analyst can be avoided or can be significantly reduced. In the peak filter, an extraction spectrum may be caused to act on the mass spectrum as a gate signal, or the extraction spectrum may be caused to mathematically act on the mass spectrum.

According to another aspect of the present disclosure, the mass spectrum processing apparatus further comprises a preprocessor provided upstream of the generator, and configured to extract a plurality of mass spectra from an overall mass spectrum, and the generator is configured to generate the simulated spectrum for each of the plurality of mass spectra.

When an entirety of the mass spectrum itself (hereinafter, also referred to as an "overall mass spectrum") obtained by the mass spectrometry is set as a unit of processing by the learned model, the learned model becomes large and complicated. With the above-described structure, such a problem can be avoided. In addition, there is another advantage that, during the learning process, a plurality of data sets for learning can be generated from one overall mass spectrum for learning.

According to another aspect of the present disclosure, the mass spectrum processing apparatus further comprises a postprocessor provided downstream of the generator, and configured to generate a combined simulated spectrum based on a plurality of simulated spectra generated from the plurality of mass spectra, and the peak filter is configured to extract the plurality of mass peaks based on the combined simulated spectrum. Alternatively, the combined simulated spectrum may be formed as a collected group of a plurality of simulated spectra.

According to another aspect of the present disclosure, in the mass spectrum processing apparatus, a high-mass-side end of a kth mass spectrum and a low-mass-side end of a (k+1)th mass spectrum are in an overlapped relationship, and the postprocessor is configured to combine the plurality of simulated spectra according to the overlapped relationship. According to this structure, a discrimination precision for peaks included at ends of the mass spectra can be increased. Here, k is an integer greater than or equal to 1.

According to another aspect of the present disclosure, in the mass spectrum processing apparatus, the peak filter is configured to extract, from among the group of mass peaks, a plurality of peaks belonging to a plurality of extraction sections determined based on the plurality of simulated peaks. For example, for each simulated peak, an extraction section extending in the m/z axis direction may be determined. Mass peaks having an apex or a center of gravity belonging to the extraction section may be extracted. A size of the extraction section may be changed according to circumstances.

According to another aspect of the present disclosure, the mass spectrum processing apparatus further comprises a peak list generator configured to generate a peak list based on the mass spectrum, and the peak filter is configured to act on the peak list. According to this structure, a judgment is made as to whether each list element in the peak list; that is, each individual mass peak, is the sample peak. Alternatively, the simulated spectrum may be caused to act on the mass spectrum itself.

According to another aspect of the present disclosure, there is provided a method of processing a mass spectrum, comprising: generating, by a learned model, a simulated spectrum for discriminating a sample-derived peak from a mass spectrum; and extracting, from among a group of mass peaks included in the mass spectrum, a plurality of mass peaks corresponding to a plurality of simulated peaks included in the simulated spectrum. The method may be realized as a function of hardware or as a function of software. In the case of the latter, a program for executing the method of processing the mass spectrum is installed on an information processor via a network or via a recording medium. The program is stored in a non-transitory recording medium provided inside or outside of the information processor. The concept of the information processor includes a computer which functions as a spectrum processing apparatus.

According to another aspect of the present disclosure, there is provided a method of generating a model, comprising: generating a plurality of mass spectra for learning, by fragmenting an overall mass spectrum for learning; generating a plurality of simulated spectra for learning having an action to discriminate a sample peak, based on the plurality of mass spectra for learning; and generating a learned model by providing the plurality of mass spectra for learning and the plurality of simulated spectra for learning to a generator as a plurality of data sets for learning, and enabling the generator to learn.

According to the structure described above, because a plurality of mass spectra for learning and a plurality of simulated spectra for learning are generated from one overall mass spectrum, the learned model can be generated even when a large number of overall mass spectra for learning cannot be prepared. The background noise peak has a tendency such that the shape reproducibility is low and the width is wide. Such a tendency can be observed over the entirety of the mass spectrum. Therefore, generation of a plurality of data sets for learning from one overall mass spectrum is permitted. In the learned model, the knowledge and the experience of the analyst are accumulated. Alternatively, such a learned model may be ported to a plurality of mass spectrum processing apparatuses.

According to another aspect of the present disclosure, the method of generating the model further comprises receiving a designation of a plurality of sample peaks included in the plurality of mass spectra for learning, and a plurality of simulated peaks included in the simulated spectrum for learning are generated based on the designation of the plurality of sample peaks, and each of the simulated peaks has a waveform for discriminating the sample peak. The designation of each sample peak is normally done by the analyst. Based on the designation, an artificial peak is generated as the simulated peak. According to another aspect of the present disclosure, the plurality of simulated peaks are of the same form.

BRIEF DESCRIPTION OF THE DRAWINGS

Embodiment(s) of the present disclosure will be described based on the following figures, wherein.

DESCRIPTION OF THE INVENTION

An embodiment of the present disclosure will now be described with reference to the drawings.

Figure 1:
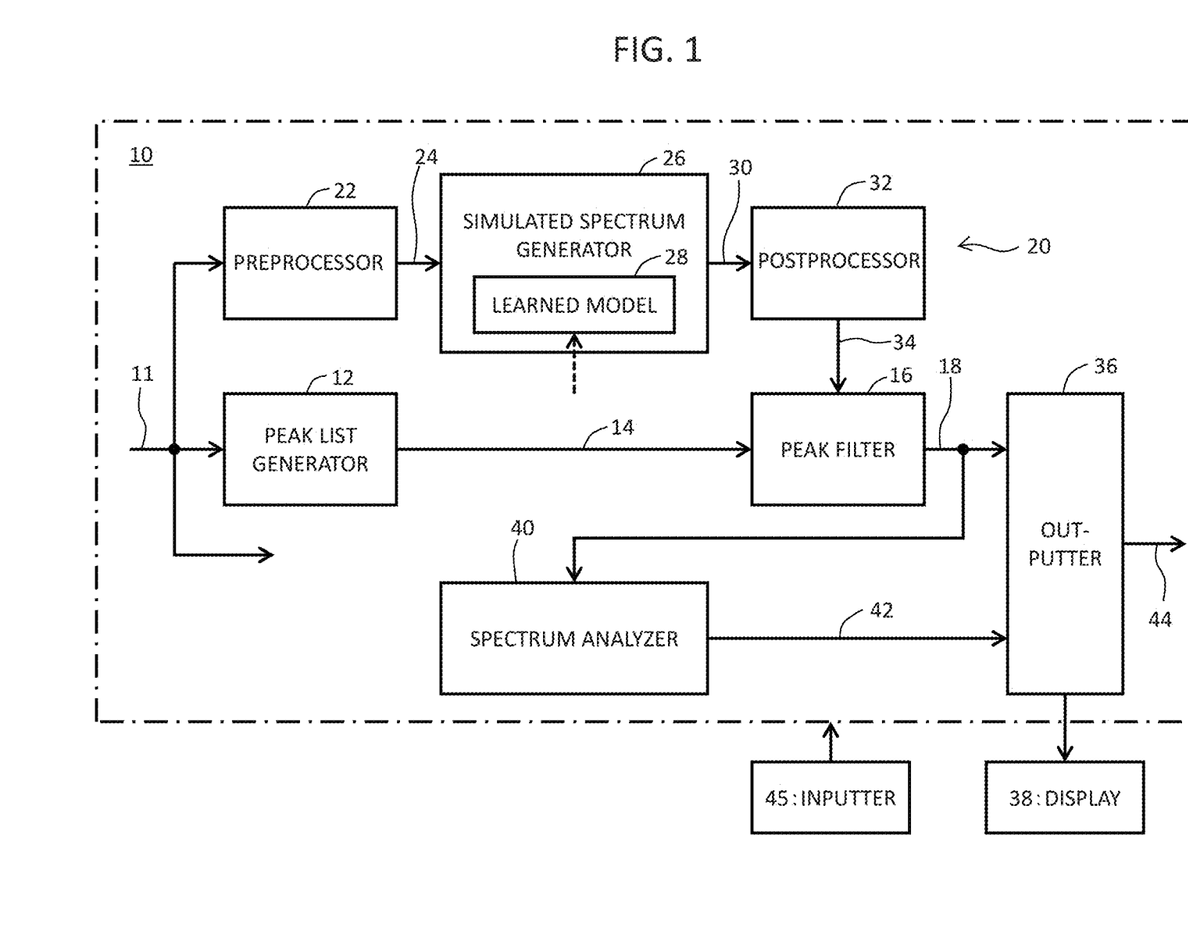
FIG. 1 is a block diagram showing a mass spectrum processing apparatus according to an embodiment of the present disclosure.

FIG. 1 is a block diagram showing an overall structure of a mass spectrum processing apparatus according to an embodiment of the present disclosure. The mass spectrum apparatus is formed from, for example, a computer serving as an information processor. Alternatively, the mass spectrum processing apparatus may be incorporated in a mass spectroscopy apparatus. In FIG. 1, the mass spectrometry apparatus is not illustrated. The mass spectrometry apparatus is formed from an ion source, a mass spectrometry unit, a detector unit, and the like. Mass spectrometry of a sample is executed by the mass spectrometry apparatus, and a mass spectrum is consequently generated. Alternatively, the mass spectrum may be generated by the mass spectrum processing apparatus based on a signal which is output from the mass spectrometry apparatus.

In FIG. 1, the mass spectrum processing apparatus comprises a computation unit 10, a display 38, and an inputter 45. The computation unit 10 is formed from, for example, a processor, and is more specifically formed from a CPU which operates according to a program. The display 38 is, for example, a liquid crystal display. The inputter 45 is, for example, a keyboard and a pointing device.

In FIG. 1, a plurality of functions of the computation unit 10 are represented as a plurality of blocks. The individual blocks will now be described in detail. An entirety of a mass spectrum to be processed (hereinafter referred to as an "overall mass spectrum") 11 is input to a generator 20 and a preprocessor 22. In addition, the overall mass spectrum 11 is also sent to an outputter 36 or the like as necessary.

A peak list generator 12 executes a peak search or a peak detection on the overall mass spectrum 11, and generates a peak list 14 including a plurality of sets of numerical value information representing a plurality of peaks included in the overall mass spectrum 11. More specifically, the peak list 14 includes a plurality of list elements corresponding to the plurality of peaks, and each list element (that is, numerical value information) is formed from information which specifies a position, an intensity, or the like of the peak, as will be shown below. The peak list 14 is sent to a peak filter 16.

In the illustrated example structure, the generator 20 is formed from the preprocessor 22, a simulated spectrum generator 26, and a postprocessor 32. The preprocessor 22 extracts a plurality of mass spectra 24 as a plurality of fragments from the overall mass spectrum 11 by fragmentation of the overall mass spectrum 11. More specifically, the plurality of mass spectra 24 are extracted with a partial overlapped relationship along an m/z axis. The plurality of mass spectra 24 are sequentially input to the simulated spectrum generator 26.

The simulated spectrum generator 26 generates one simulated spectrum 30 from one mass spectrum 24. The simulated spectrum generator 26 is formed from, for example, a CNN (Convolutional Neural Network). The simulated spectrum generator 26 has a learned model 28. A substance of the learned model 28 is a CNN parameter set; that is, a numerical value set. Alternatively, the simulated spectrum generator 26 may be formed from a mechanical learning type generator other than the CNN. A model generating apparatus and a model generation method for generating the learned model 28 will be described later with reference to FIG. 2 or the like.

The mass spectrum 24 normally includes a plurality of mass peaks. More specifically, the mass spectrum 24 includes a plurality of sample peaks and a plurality of background noise peaks. In order to extract the plurality of sample peaks and remove the plurality of background noise peaks, the simulated spectrum 30 having a peak discriminating action is generated. Specifically, the simulated spectrum 30 includes a plurality of simulated peaks for extracting the plurality of sample peaks. In generation of the plurality of simulated peaks, in the present embodiment, a mechanical learning type generator is used, as already described. With this configuration, manual peak discriminating work with respect to the overall mass spectrum 11 or with respect to each mass spectrum 24 becomes unnecessary.

The postprocessor 32 combines the plurality of simulated spectra 30 which are sequentially generated, to generate a combined simulated spectrum 34 corresponding to the overall mass spectrum 11. The plurality of simulated spectra 30 are combined based on a combining rule corresponding to a fragmenting rule in the preprocessor 22. The fragmentation and the combination will be described later in detail.

The peak filter 16 causes the combined simulated spectrum 34 to act on the peak list 14, to generate a selected peak list 18. As will be described later, a plurality of extraction sections are set on the m/z axis based on the plurality of simulated peaks included in the combined simulated spectrum 34, and a plurality of mass peaks belonging to the plurality of extraction sections are extracted as a plurality of sample peaks. In this process, for example, a determination is made as to whether or not coordinates of a center of gravity or an apex of each mass peak belong to any of the extraction sections. The selected peak list 18 is sent to the outputter 36, and is also sent to a spectrum analyzer 40.

The outputter 36 functions as a display processor and an output processor. The display 38 is connected to the outputter 36. On the display 38, the overall mass spectrum 11, the selected peak list 18, an analysis result 42 of the spectrum analyzer 40 to be described below, and the like are displayed. Alternatively, on the display 38, the plurality of mass spectra 24, the plurality of simulated spectra 30, the combined simulated spectrum 34, or the like may be displayed. Alternatively, data 44 may be transferred from the outputter 36 to an external device via a network.

The spectrum analyzer 40 is a module which analyzes a peak list or the mass spectrum after filtering. The spectrum analyzer 40 has a function to execute Kendrick mass defect analysis, to be described later. The analysis result 42 is sent to the outputter 36.

Figure 2:
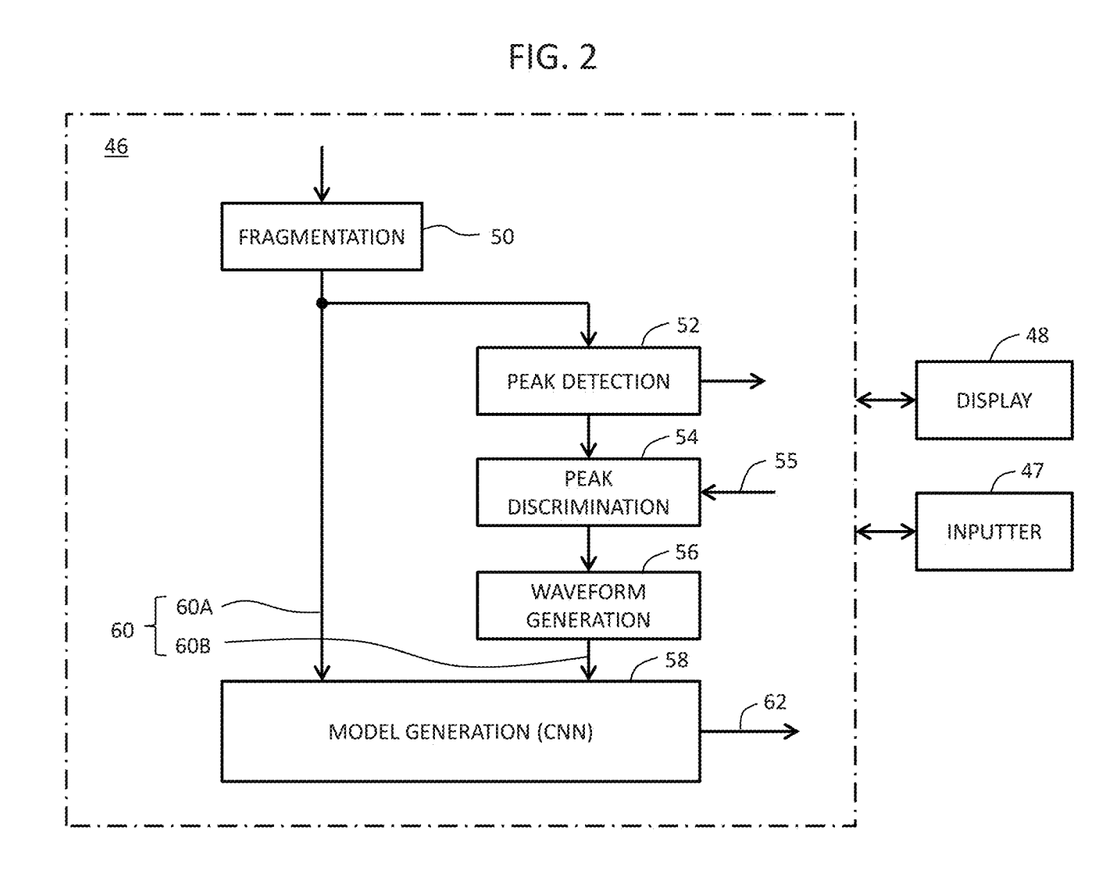
FIG. 2 is a block diagram showing a model generating apparatus according to an embodiment of the present disclosure.

FIG. 2 is a block diagram showing an example configuration of a model generating apparatus according to an embodiment of the present disclosure. The model generating apparatus is an apparatus which generates the learned model shown in FIG. 1. The model generating apparatus is formed from an information processor, and is, for example, a computer. The information processor shown in FIG. 1 and the information processor shown in FIG. 2 are normally separate apparatuses, but may alternatively be integrated.

The model generating apparatus has a computation unit 46, an inputter 47, and a display 48. The computation unit 46 is formed from, for example, a processor, and is more specifically formed from a CPU which operates according to a program. The inputter 47 is formed from, for example, a keyboard and a pointing device. The display 48 is formed from, for example, a liquid crystal display.

In FIG. 2, a plurality of steps of a method of generating a model executed by the computation unit 46 are represented by a plurality of blocks. With fragmentation 50 of an overall mass spectrum for learning which is input, a plurality of mass spectra for learning are generated. Each mass spectrum for learning is formed from, for example, 1024 numerical values. Of these values, a low-mass-side end (for example, 20 consecutive numerical values) and a high-mass-side end (for example, 20 consecutive numerical values) are overlapped portions.

For each mass spectrum for learning, peak detection 52 is applied. In this process, a known technique for automatically detecting the peak is used. Alternatively, a peak detection condition may be set by the analyst using the inputter 47. As a result of the peak detection 52, a peak list is constructed. Contents of the peak list are displayed on the display 48.

For each list element of the peak list; that is, for each peak, the analyst judges whether the peak is the sample peak or the background noise peak by a visual inspection (refer to reference numeral 54). In this process, the inputter 47 is used (refer to reference numeral 55). For example, the sample peaks are designated by the analyst. Alternatively, the plurality of sample peaks may be indirectly designated by designating the background noise peaks. In the designation of the sample peak, reference is made to a peak form, as well as to information such as an m/z value (for example, m/z of the center of gravity), the intensity (for example, a peak area), and a peak width (half width).

In waveform generation 56, a predetermined waveform is generated for each designated peak. For example, the same waveform having a certain height is generated. For example, functions such as normal distribution (Gaussian function), or figures such as an isosceles triangle, or the like are generated. In the present embodiment, a normal distribution having a predetermined half width is generated. Thus, each sample peak included in the mass spectrum is replaced with a predetermined waveform having a certain height. In this process, a width of the predetermined waveform may be set larger than the width of the designated peak. Alternatively, the width may be set variable. With the designation of the plurality of sample peaks; that is, the plurality of simulated peak positions, the plurality of background noise peaks in the mass spectrum are discarded. As a result of the waveform generation 56, the simulated spectrum is generated.

Learning data 60 sequentially provided to a generator 58 which generates the model are formed from a mass spectrum 60A caused by the fragmentation 50, and a simulated spectrum 60B generated based on the mass spectrum 60A. The CNN parameter set is improved so that the latter becomes closer to the former. For example, from one mass spectrum, a few, a few tens, a few hundreds, or a few thousands of learning data sets are obtained. Normally, a necessary number of data sets for learning 60 are generated based on a plurality of mass spectra. A learned model 62 generated after a sufficient learning process is provided to one or a plurality of mass spectrum processing apparatuses. For example, for the generation of the learned model 62, one thousand or more sample peaks are used.

Figure 3:
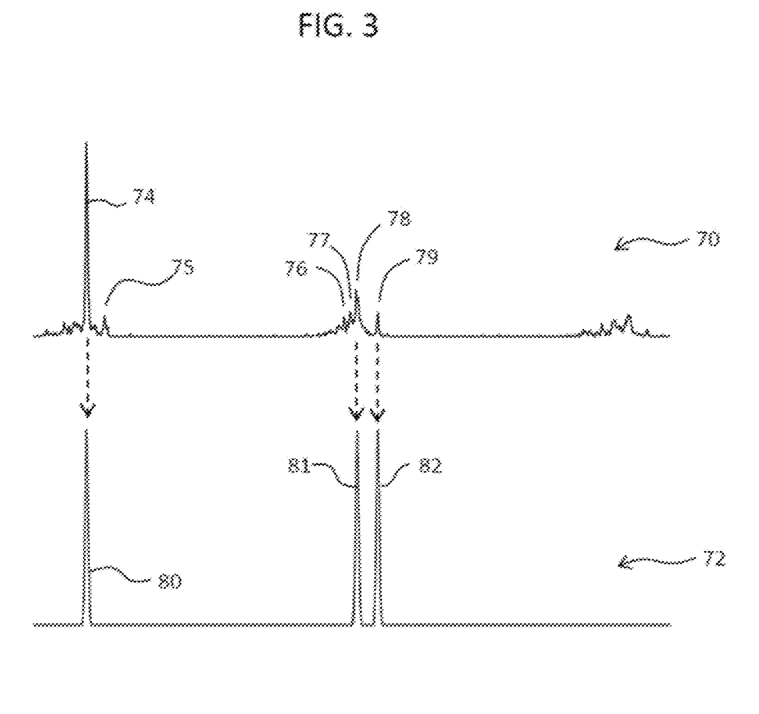
FIG. 3 is a diagram showing a relationship between a mass spectrum for learning and a simulated spectrum for learning.

FIG. 3 exemplifies a mass spectrum for learning (more accurately, a part thereof) 70, and a simulated spectrum for learning (more accurately, a part thereof) 72. The simulated spectrum for learning 72 is generated from the mass spectrum for learning 70. For example, a case may be exemplified in which the mass spectrum 70 includes a plurality of mass peaks 74~79 (and also includes other mass peaks) and, of these, the mass peaks 74, 78, and 79 are sample peaks. In this case, a simulated spectrum 72 includes simulated peaks 80, 81, and 82 corresponding to the mass peaks 74, 78, and 79. The simulated peaks 80, 81, and 82 have a similar, steep form. The simulated spectrum 72 does not include a simulated peak corresponding to the background noise peak. The mass spectrum 70 and the simulated spectrum 72 shown in FIG. 3 are provided to the mechanical learning type generated as the learning data.

Figure 4:
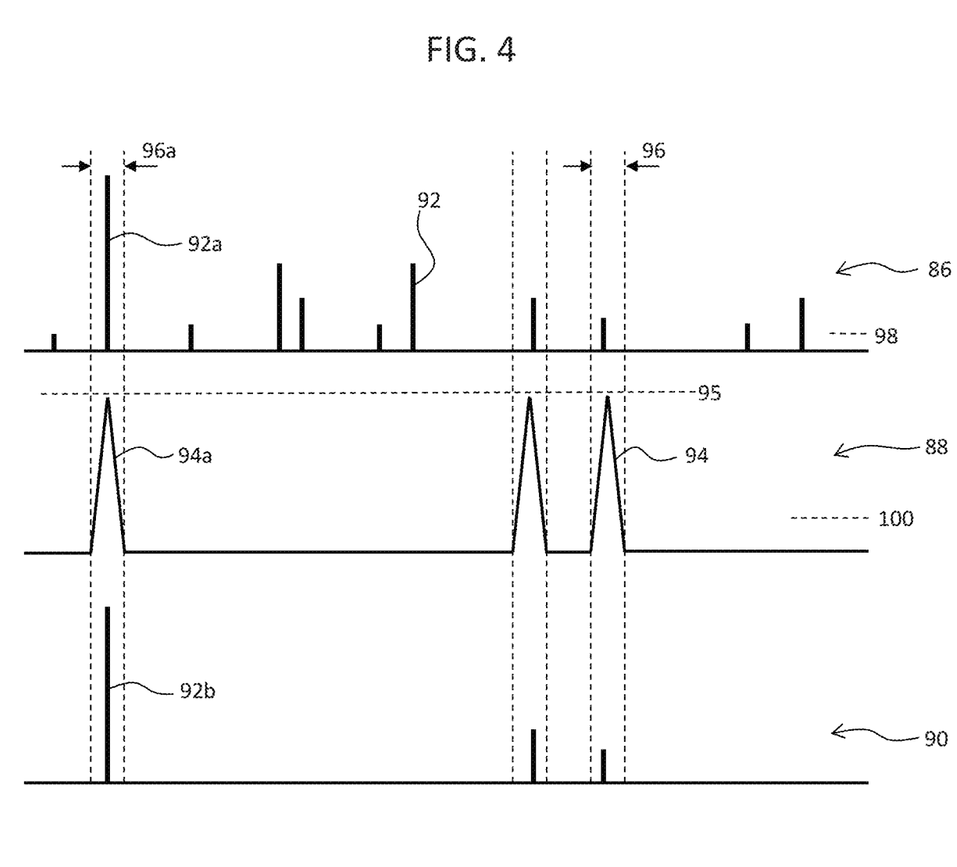
FIG. 4 is a diagram showing an action of a peak filter.

FIG. 4 schematically and conceptually shows a process at the peak filter. FIG. 4 shows at an upper portion a mass spectrum 86, at a middle portion a simulated spectrum 88, and at a lower portion a mass spectrum after filtering 90. In reality, the peak list is processed by the peak filter.

The simulated spectrum 88 is generated from the mass spectrum 86 itself, which is the processing target. In this process, the mechanical learning type generator functions. The mass spectrum 86 includes a plurality of mass peaks 92. The simulated spectrum 88 includes a plurality of simulated peaks 94 for discriminating peaks derived from the sample. For each simulated peak 94, an extraction section 96 is set as a section between the ends of the simulated peak 94. Among the plurality of peaks 92 included in the mass spectrum 86, a mass peak having a center of gravity belonging to any of the extraction sections 96 is set as the extraction target. For example, an extraction section 96a is set by a simulated peak 94a, and a mass peak 92a having the center of gravity included in the extraction section 96a is determined and is extracted. The mass spectrum 90 after filtering 90 includes a mass peak 92b corresponding to the mass peak 92a which is set as the extraction target.

In the process described above, a height 95 of the simulated peak 94 is not directly used, and a width of the simulated peak 94 is used. The simulated peak 94 may be artificial generated using various functions or figures which can define the width. Alternatively, the height of the simulated peak 94 may be used for weighting.

Alternatively, a preprocess using a threshold 98 may be applied to the mass spectrum 86. For example, peaks which are smaller than the threshold 98 may be removed beforehand. Desirably, a configuration is employed so that the threshold 98 may be varied. Alternatively, a threshold 100 may be set with respect to the simulated spectrum 88, and a width defined by the threshold 100 may be determined as the extraction section. In this case, because each simulated peak has a pinnacle shape, a size of each extraction section can be varied by changing the threshold 100.

Figure 5:
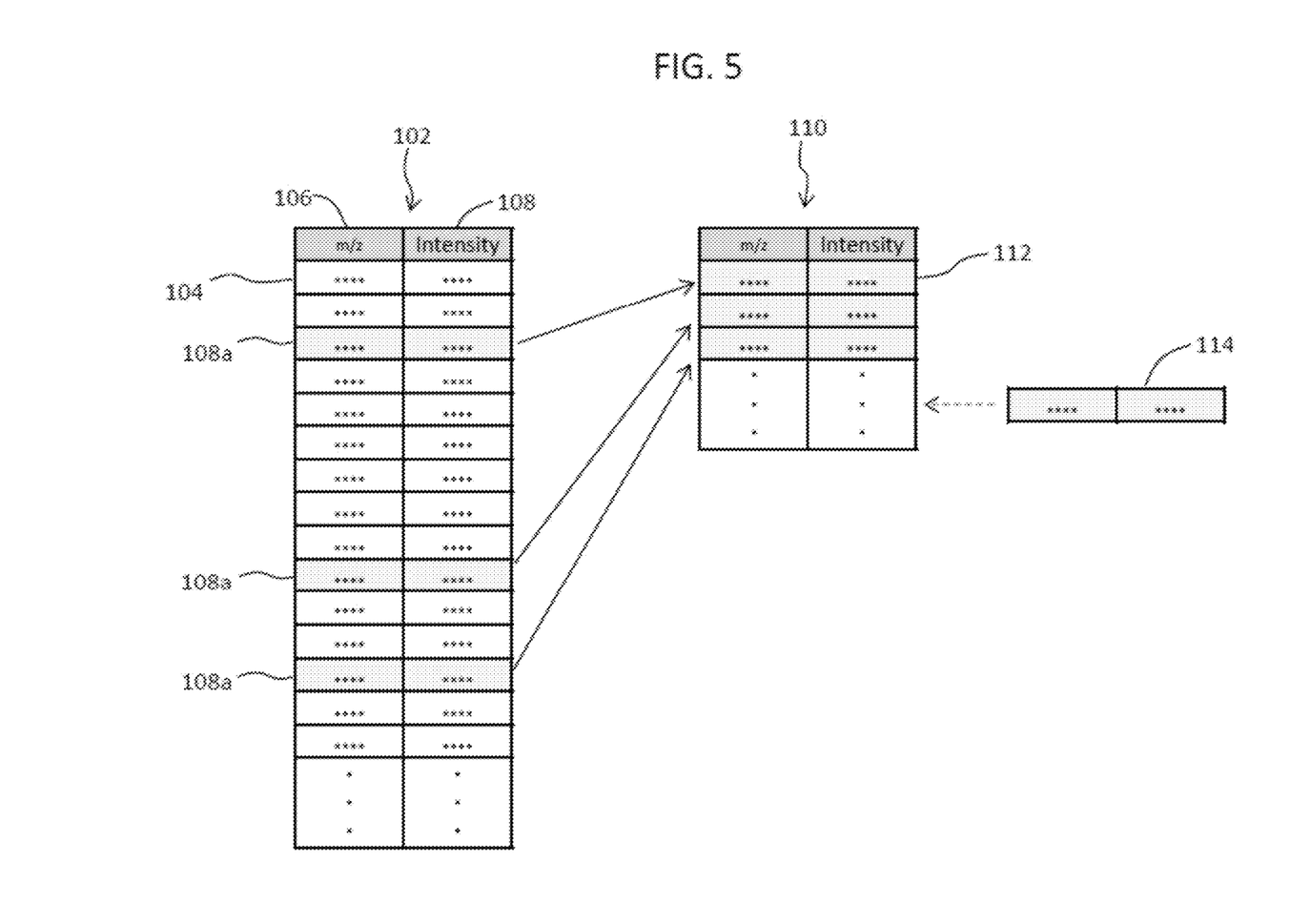
FIG. 5 is a diagram showing generation of a selected peak list by a peak filter.

FIG. 5 shows specifics of the process executed by the peak filter. A peak list 102 is generated based on the mass spectrum. The peak list 102 includes a plurality of list elements 104 corresponding to a plurality of peaks. Each list element 104 includes a numerical value showing an m/z value 106, and a numerical value showing an intensity 108. Alternatively, the list element 104 may further include numerical values of the half width, a resolution, or the like. Reference numeral 108a shows a peak (list element) extracted by an action of the simulated spectrum. A selected peak list 110 is a peak list after the filtering. The selected peak list 110 includes a plurality of list elements 112 showing the sample peak. In addition to a selection from the peak list 102, the selected peak list 110 may be generated by adding a list element 114.

Figure 6:
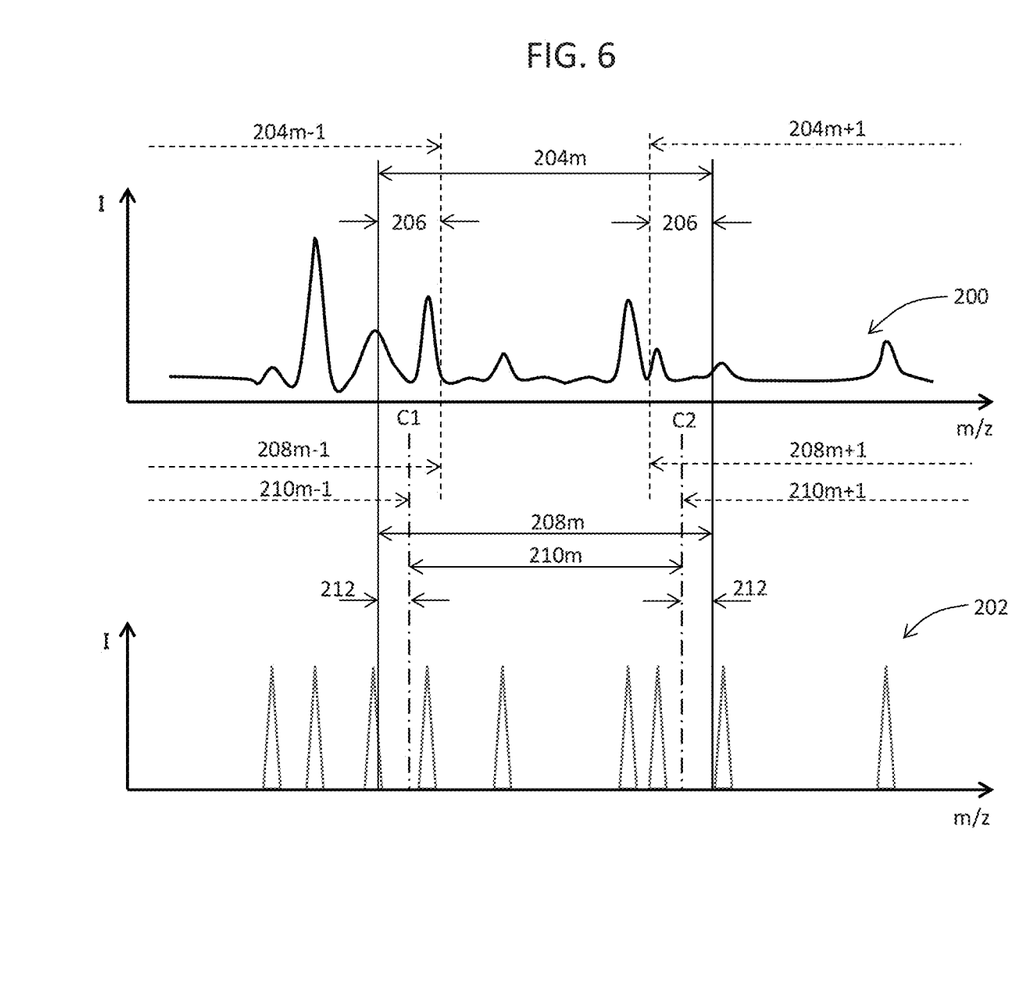
FIG. 6 is a diagram showing contents of a preprocess and a postprocess.

FIG. 6 exemplifies processes executed by the preprocessor and the postprocessor. A plurality of mass spectra $204m-1$, $204m$, and $204m+1$ are extracted from an overall mass spectrum 200. Here, m is an integer, and m−1, m, and m+1 show a sequence order. An overlapped portion 206 is generated over two adjacent mass spectra. That is, for example, a high-mass-side end of the mass spectrum $204m$ and a low-mass-side end of the adjacent mass spectrum $204m+1$ overlap each other.

A plurality of simulated spectra $208m-1$, $208m$, and $208m+1$ are generated based on the plurality of mass spectra $204m-1$, $204m$, and $204m+1$. A combined simulated spectrum 202 is generated by combining the plurality of simulated spectra $208m-1$, $208m$, and $208m+1$. In this process, each overlapped portion 206 is processed as follows.

In each simulated spectrum (for example, the simulated spectrum $208m$), a half 212, in the overlapped portion at the low-mass side, exceeding a center position C1 in the low-mass side, and a half 212, in the overlapped portion at the high-mass side, exceeding a center position C2 in the high-mass side are not used in the peak filter process. A section where the function of the simulated spectrum $208m$ is actually realized is a section $210m$. Similarly, in the two simulated spectra $208m-1$ and $208m+1$ adjacent on the low-mass side and high-mass side, respectively, the sections in which the functions of the simulated spectra are realized are sections $210m-1$ and $210m+1$.

For the plurality of simulated spectra $208m-1$, $208m$, and $208m+1$ as a whole, there is no gap in which the filtering cannot be executed. Such an adjustment of the overlapped portions is the substance of the above-described combining process, and a result of such an adjustment is the combined simulated spectrum 202. It is not necessary to further execute a process to physically or electronically integrate the plurality of simulated spectra 208*m*−1, 208*m*, and 208*m*+1. When the simulated peak exists over two sections, the simulated peaks may be divided and distributed to the two sections, or one of the sections may be expanded.

Each of the mass spectra and the simulated spectra is formed from, for example, 1024 numerical values. Of these numerical values, the ends are formed from, for example, 20 numerical values. The numerical values described in the present specification are merely exemplary.

Figure 7:
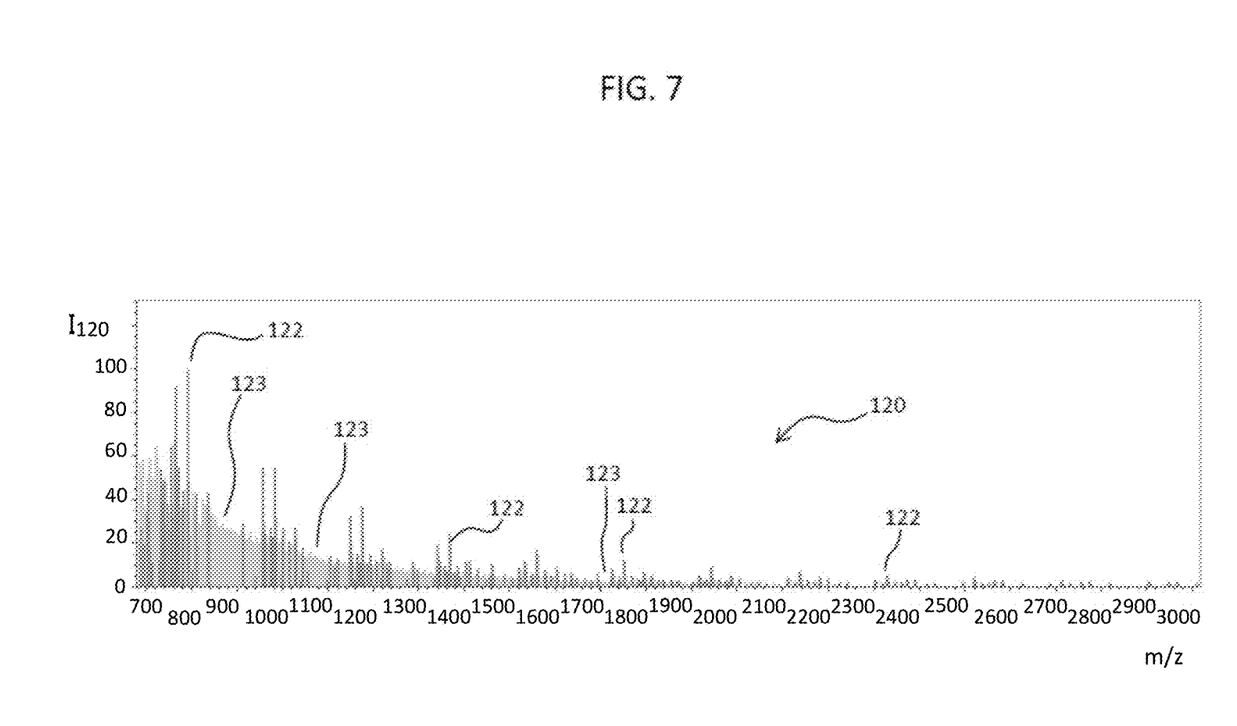
FIG. 7 is a diagram showing a mass spectrum.

FIG. 7 exemplifies a mass spectrum. In a mass spectrum 120 which is illustrated, a plurality of sample peaks specified by the peak discrimination according to the present embodiment are drawn dark (refer to reference numeral 122), and a plurality of peaks which are not targets of peak discrimination are drawn lightly (refer to reference numeral 123). The plurality of peaks which are drawn lightly are understood to be the background noise peaks.

Figure 8:
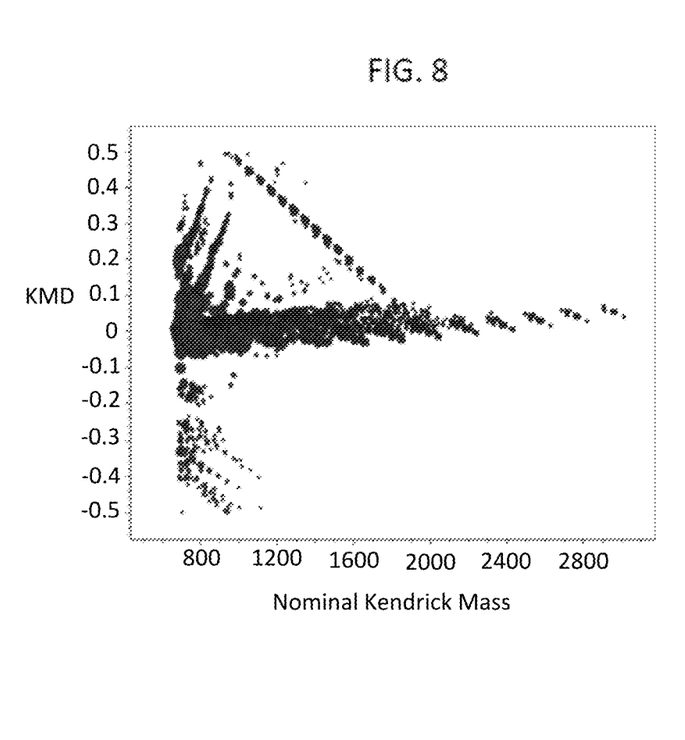
FIG. 8 is a diagram showing a result of Kendrick mass defect analysis in a case where mass spectrum processing according to an embodiment of the present disclosure is not executed.
Figure 9:
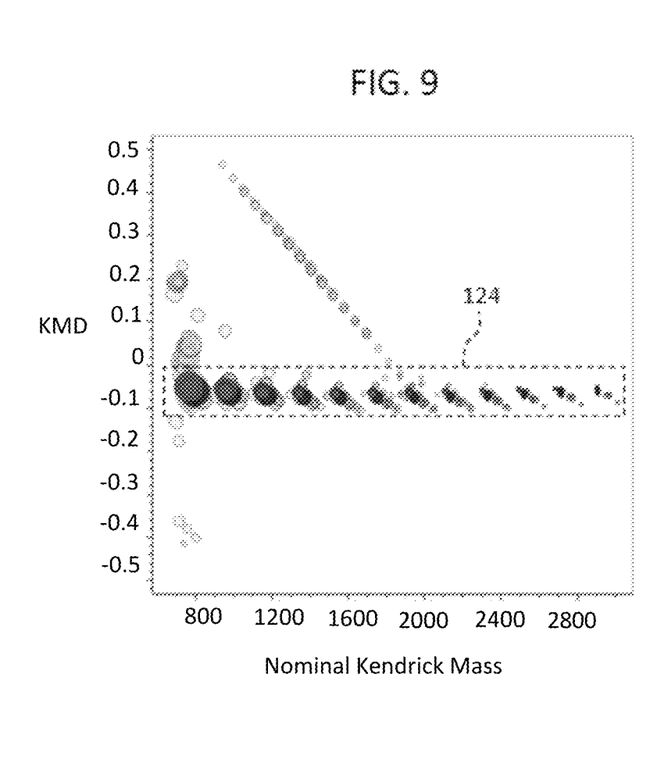
FIG. 9 is a diagram showing a result of Kendrick mass defect analysis in a case where the mass spectrum processing according to an embodiment of the present disclosure is executed.

FIGS. 8 and 9 show a result of analysis of the mass spectrum shown in FIG. 7. More specifically, FIG. 8 shows a result of Kendrick mass defect analysis based on a mass spectrum before the spectrum processing of the present embodiment is applied, and FIG. 9 shows a result of the Kendrick mass defect analysis based on a mass spectrum after the spectrum processing of the present embodiment is applied. In distributed diagrams shown in FIGS. 8 and 9, a horizontal axis shows a NKM to be described below, and a vertical axis shows a KMD to be described below. In FIG. 9, a polymer series 124 can be clearly seen.

The Kendrick mass defect analysis will now be described. A Kendrick mass KM of a molecule having a certain mass M is defined as follows.

$$KM = M \times 14/14.01565 \qquad \text{(Equation 1)}$$

In Equation 1 described above, a mass of $^{12}C^1H_2$ is set as 14. The value of 14.01565 is an IUPAC mass of $CH_2$. When the molecule having the mass M is formed as a chain of repeating units of $CH_2$, the mass M can be represented as follows.

$$M = (14.01565) \times n + \alpha \qquad \text{(Equation 2)}$$

Here, n is a number of the repeating units forming the repetitious structure, and a is a mass of portions other than the repetitious structure. When Equation 2 is substituted into Equation 1, the following can be obtained.

$$KM = 14 \times n + 14/14.01565 \times \alpha \qquad \text{(Equation 3)}$$

An integer portion of KM is set as integer KM (nominal Kendrick mass, NKM), and a value obtained by subtracting KM from NKM is set as a Kendrick mass defect (KMD).

Figure 10:
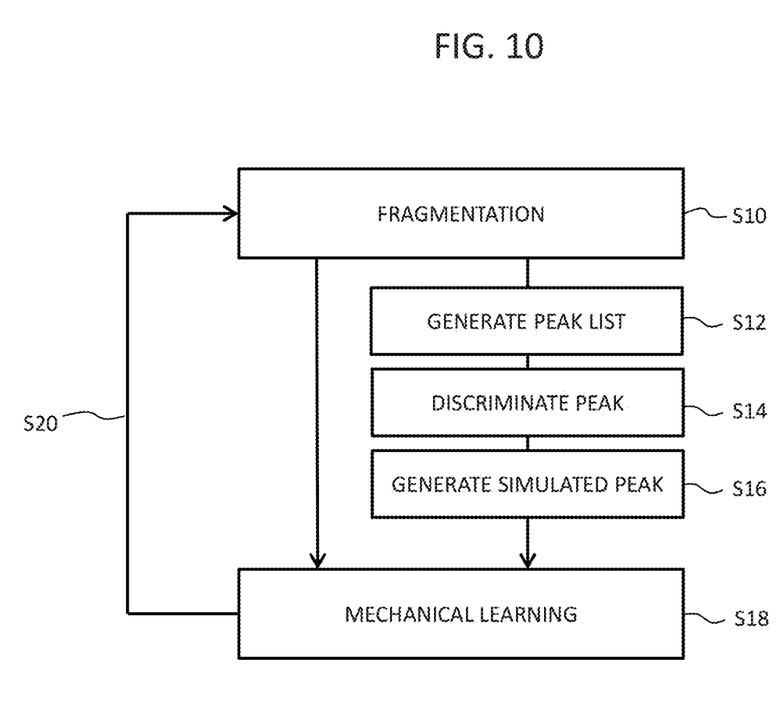
FIG. 10 is a flowchart showing a method of generating a model according to an embodiment of the present disclosure.

FIG. 10 shows a method of generating a model according to the present embodiment as a flowchart. In S10, a mass spectrum is generated by fragmenting the overall mass spectrum. In S12, peak search is executed on the mass spectrum, and the peak list is generated. Alternatively, S12 may be executed prior to S10. In S14, a plurality of sample peaks are designated from a plurality of mass peaks in the peak list. The designation is done by an analyst having knowledge and experience in mass spectrum analysis. As a result of the designation, a selected peak list formed from a plurality of sample peaks is generated. In S16, the simulated spectrum is generated based on the selected peak list. In this process, a predetermined waveform is generated for each sample peak. In S18, one mass spectrum generated by the fragmentation and one simulated spectrum generated based on the one mass spectrum are provided to the generator as one data set for learning, and the learning is executed. As shown by S20, the above-described process is repeated for each mass spectrum.

With the above, the learned model is generated. The learned model is ported to one or a plurality of spectrum analyzing apparatuses. Alternatively, the learned model may be uploaded on cloud on the Internet, and may be downloaded from the cloud to a plurality of spectrum processing apparatuses.

Figure 11:
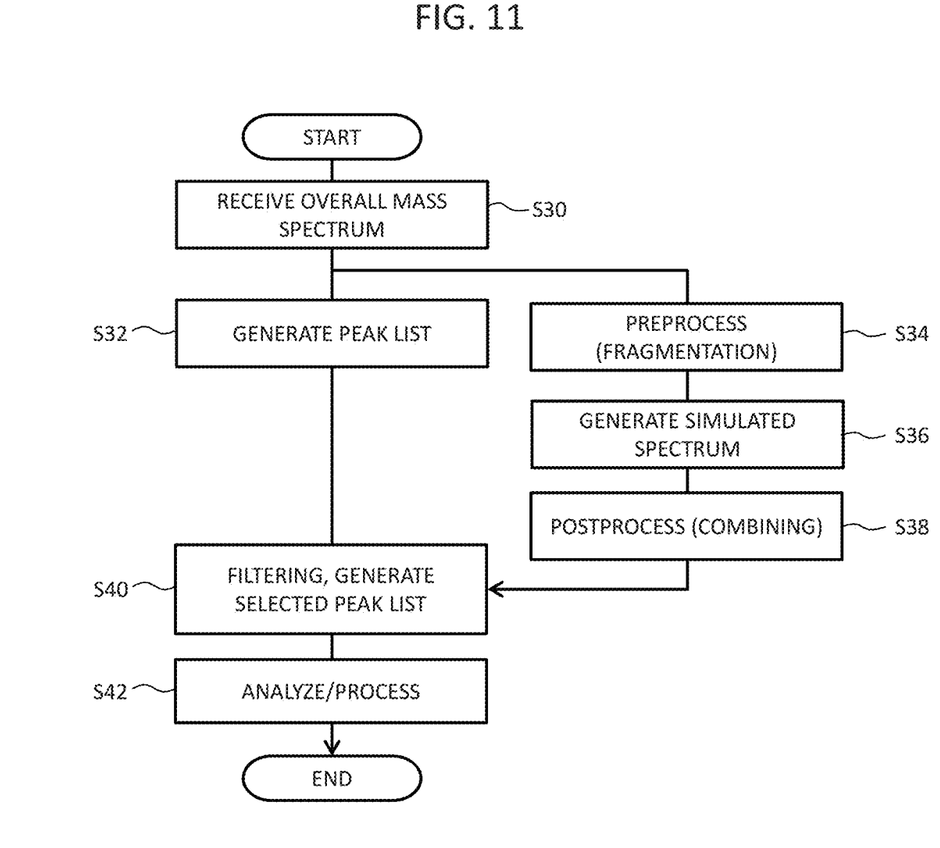
FIG. 11 is a flowchart showing a method of processing a mass spectrum according to an embodiment of the present disclosure.

FIG. 11 shows a method of processing a mass spectrum as a flowchart. In S30, the overall mass spectrum is provided to the mass spectrum processing apparatus. In S32, a peak list is generated by peak search on the overall mass spectrum. In S34, a plurality of mass spectra are sequentially generated by fragmenting the overall mass spectrum. In S36, a simulated spectrum is generated for each mass spectrum by the learned model. In S38, a combined simulated spectrum is generated based on the plurality of simulated spectra. In S40, the peak list is filter-processed based on the combined simulated spectrum, and the selected peak list is thereby generated. In S42, analysis or the like of the selected peak list is executed.

Figure 12:
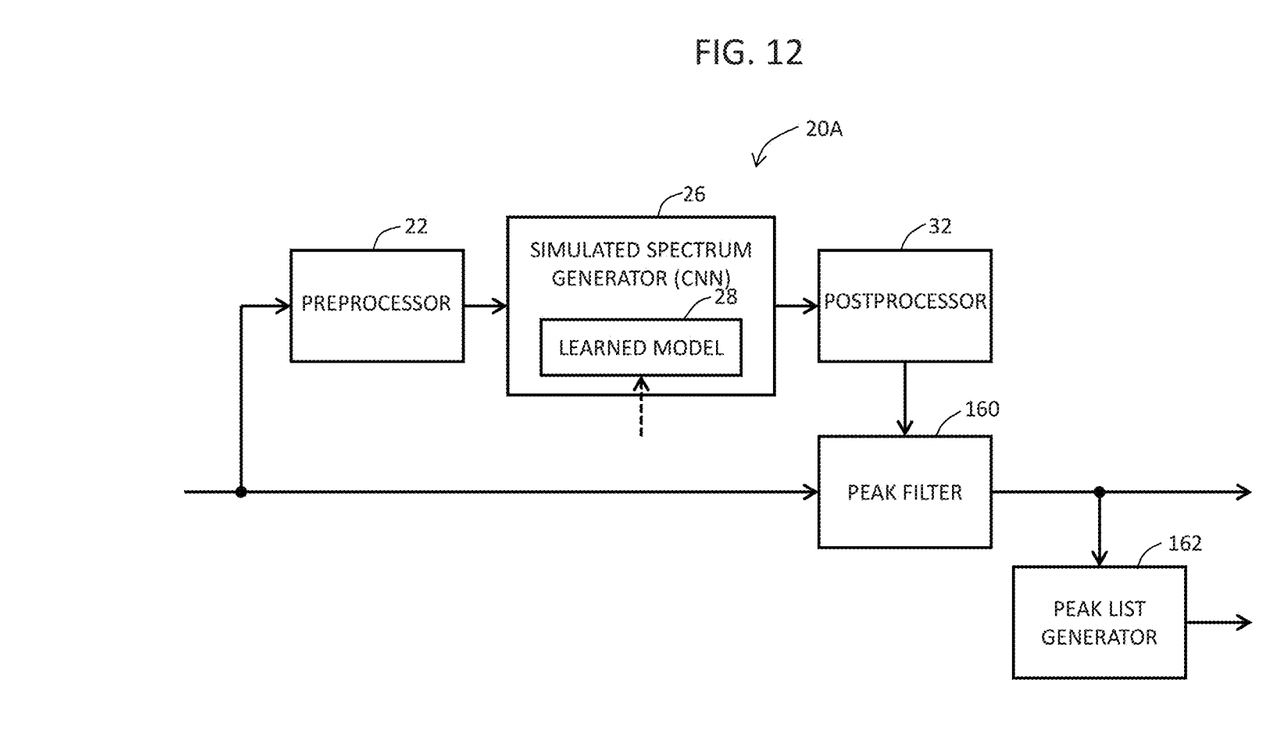
FIG. 12 is a block diagram showing a first alternative configuration.

FIG. 12 shows a first alternative configuration of the mass spectrum processing apparatus. FIG. 12 is a block diagram showing relevant portions of the mass spectrum processing apparatus. The peak list generator is not provided upstream of a peak filter 160, and a peak list generator 162 is provided downstream of the peak lifter 160. Similar to the generator shown in FIG. 1, a generator 20A is formed from the preprocessor 22, the simulated spectrum generator 26 having the learned model, and the postprocessor 32. In the first alternative configuration, a filtering process is applied on the overall mass spectrum in the peak filter 160. For example, portions other than the plurality of sample peaks are suppressed. As necessary, the peak list is generated from the overall mass spectrum after the filtering process, by the peak list generator 162. When a filtering process of the overall mass spectrum itself is necessary, the first alternative configuration is desirably employed. Alternatively, on the overall mass spectrum, the plurality of sample peaks which are discriminated may be represented in an identifiable manner by a specifying color or a specifying marker.

Figure 13:
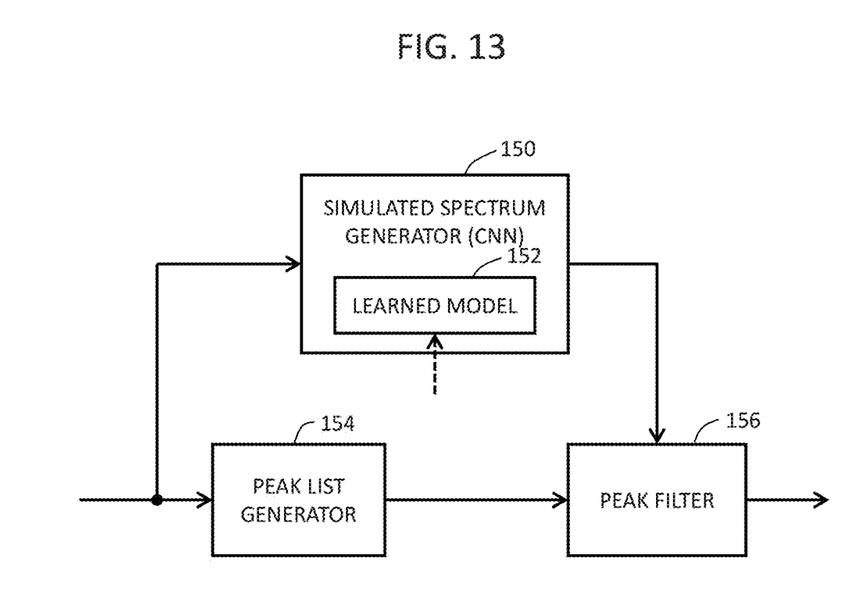
FIG. 13 is a block diagram showing a second alternative configuration.

FIG. 13 shows a second alternative configuration of the mass spectrum processing apparatus. FIG. 13 is a block diagram showing relevant portions of the mass spectrum processing apparatus. In the second alternative configuration, the fragmentation of the mass spectrum is not executed, and the overall mass spectrum is provided to a simulated spectrum generator 150 having a learned model 152. A large simulated spectrum corresponding to the overall mass spectrum is generated by the simulated spectrum generator 150, and is provided to a peak filter 156. A filtering process with respect to a peak list generated by a peak list generator 154 is executed in the peak filter 156, and a plurality of sample peaks are thereby extracted. When a number of data sets of the overall mass spectrum is small, the second alternative configuration is desirably employed.

In the present embodiment described above, it is possible to cause a generator to mechanically learn the knowledge of peak discrimination based on a difference between a form of the sample peak and a form of the background noise peak, and to thereby generate the learned model. By generating the simulated spectrum from the mass spectrum using such a learned model, highly reliable filtering information can be obtained. In this process, the burden on the work for the analyst or the like basically is not imposed.

Alternatively, while executing the filtering on the mass spectrum, a re-learning of the model may be caused in parallel to the filtering, to generate a better learned model. In this case, complementary correction by the analyst may be executed on the peak list or the mass spectrum after the filtering.

With the manual discrimination by the analyst, the discriminating result may vary depending on the knowledge and the experience of the analyst. Further, the judgment may vary even for the same peak. With the above-described embodiment, an advantage can be obtained in that the peak discrimination can be stably executed.

When a number of points forming a mass peak differs depending on a position on the m/z axis, an interpolation process or a thinning process may be applied on the mass spectrum so that the number of points of the mass peak is the same at any position.

The invention claimed is:

1. A mass spectrum processing apparatus comprising:
   a generator configured to generate, by a learned model, a simulated spectrum for discriminating one or more sample peaks from a mass spectrum; and
   a peak filter configured to extract, from among a group of mass peaks included in the mass spectrum, a plurality of mass peaks corresponding to a plurality of simulated peaks included in the simulated spectrum, and to remove a plurality of noise peaks from the group of mass peaks.

2. The mass spectrum processing apparatus according to claim 1, further comprising:
   a preprocessor provided upstream of the generator, and configured to extract a plurality of mass spectra from an overall mass spectrum, wherein
   the generator is configured to generate the simulated spectrum for each of the plurality of mass spectra.

3. The mass spectrum processing apparatus according to claim 2, further comprising:
   a postprocessor provided downstream of the generator, and configured to generate a combined simulated spectrum based on a plurality of simulated spectra generated from the plurality of mass spectra, wherein
   the peak filter is configured to extract the plurality of mass peaks based on the combined simulated spectrum.

4. The mass spectrum processing apparatus according to claim 3, wherein
   a high-mass-side end of a kth mass spectrum and a low-mass-side end of a (k+1)th mass spectrum are in an overlapped relationship, and
   the postprocessor is configured to combine the plurality of simulated spectra according to the overlapped relationship.

5. The mass spectrum processing apparatus according to claim 1, wherein
   the peak filter is configured to extract, from among the group of mass peaks, a plurality of mass peaks belonging to a plurality of extraction sections determined based on the plurality of simulated peaks.

6. The mass spectrum processing apparatus according to claim 1, further comprising
   a peak list generator configured to generate a peak list based on the mass spectrum, wherein
   the peak filter is configured to act on the peak list.

7. A non-transitory recording medium storing a program for executing a method of processing a mass spectrum in an information processor, the method of processing a mass spectrum comprising:
   generating, by a learned model, a simulated spectrum for discriminating one or more sample peaks from a mass spectrum; and
   extracting, from among a group of mass peaks included in the mass spectrum, a plurality of mass peaks corresponding to a plurality of simulated peaks included in the simulated spectrum, and to remove a plurality of noise peaks from the group of mass peaks.

8. A method of generating a model, comprising:
   generating a plurality of mass spectra for learning, by fragmenting an overall mass spectrum for learning;
   generating a plurality of simulated spectra for learning having an action to discriminate a sample peak, based on the plurality of mass spectra for learning; and
   generating a learned model by providing the plurality of mass spectra for learning and the plurality of simulated spectra for learning to a generator as a plurality of data sets for learning, and enabling the generator to learn.

9. The method of generating the model according to claim 8, further comprising:
   receiving a designation of a plurality of sample peaks included in the plurality of mass spectra for learning, wherein
   a plurality of simulated peaks included in the simulated spectrum for learning are generated based on the designation of the plurality of sample peaks, and
   each of the simulated peaks has a waveform for discriminating the sample peak.

10. The method of generating the model according to claim 9, wherein
    the plurality of simulated peaks are of the same form.

* * * * *